United States Patent [19]

Grandi et al.

[11] Patent Number: 5,652,116

[45] Date of Patent: Jul. 29, 1997

[54] METHOD FOR GENETICALLY MANIPULATING PEPTIDE SYNTHETASES

[75] Inventors: Guido Grandi, Segrate; Francesca De Ferra, Lodi; Giuliano Galli, Monterotondo; Paola Cosmina, Milan, all of Italy

[73] Assignee: Eniricerche S.p.A., Milan, Italy

[21] Appl. No.: 268,542

[22] Filed: Jul. 6, 1994

[30] Foreign Application Priority Data

Jul. 13, 1993 [IT] Italy .................. MI93A1534

[51] Int. Cl.$^6$ .................. C12P 21/02; C12N 9/00
[52] U.S. Cl. .................. 435/69.1; 435/172.3; 435/183
[58] Field of Search .................. 435/183, 69.1, 435/172.3

[56] References Cited

PUBLICATIONS

Cosmina, P., et. al. (1993) Mol. Microbiol. 8(5), 821–831.
Vosman, B. et. al. (1986) Mol. Gen. Genet. 204, 524–531.
Vollenbroich, D., et al. (1993) FEBS Lett. 325(3), 220–224.
Galli, G., et. al. (1994) Bio Chim. Bio Phys. Acta 1205, 19–28.
Nakano, M.M. et. al. (1991) J. Bacteriol. 173(5), 1770–1778.
Vollenbroich, D., et. al. (1994) J. Bacteriol 176(2), 395–400.
D'Souza, C., et. al. (1993) J. Bacteriol. 175(11), 3502–3510.
Bellini, A.V., et. al. (1988) Gene 69, 325–330.
Stachelhaus, T, et. al. (1995) Science 269, 69–72.
Kleinkauf, H, et. al. (1990) Eur. J. Biochem. 192, 1–15.
Van Sinderen, D., et. al. (1993) Mol. Microbiol. 8(5), 833–841.
Borchert, S., et. al. (1992) FEMS Microbiol. Lett. 92, 175–180.

*Primary Examiner*—Charles L. Patterson, Jr.
*Attorney, Agent, or Firm*—Oblon, Spivak, McClelland, Maier & Neustadt, P.C.

[57] ABSTRACT

Disclosed is a novel method for the in vivo and in vitro synthesis of modified peptides, using either engineered microorganisms capable of expressing peptide synthetases with modified substrate specificity, or peptide synthetases extracted from said microorganisms.

7 Claims, 8 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

GCAGCGATTA TGAAGGACCG CTCAGTAGAA AC    3 2

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CATATGTTTC GCTCCCGCCT TCTGTAATTC     30

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TCTGATCGAC CGCGAGTATG GCGGCTCTAT     30

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TTTGAGATGC ATCATTTGAT TTCTGAC     27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ACAGCACGCC GAGACAGAAA ATTCACG     27

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAACCGTTTG CAAAGCTTTT CTG     23

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TGCGCAGAGC ATCAGCTTTG CCTGCTTCT     29

( 2 ) INFORMATION FOR SEQ ID NO:8:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

ACAGCACGCC GAGACAGAAA ATTCACG                    27

( 2 ) INFORMATION FOR SEQ ID NO:9:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

AGCTCCTTCA GCCAATGCTC TTCTTGC                    27

( 2 ) INFORMATION FOR SEQ ID NO:10:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:10:

CGCCTTCTCT GGATCAGCCG CAGCATCTTC                 30

METHOD FOR GENETICALLY MANIPULATING PEPTIDE SYNTHETASES

BACKGROUND OF THE INVENTION

1. Field of the Invention

The present invention relates to a method for the biological synthesis of peptides by the genetic manipulation of peptide synthetases.

In particular, the present invention relates to the construction of engineered microorganisms capable of expressing peptide synthetases with a modified substrate specificity.

The present invention also relates to the use of said microorganisms and peptide synthetases extracted from the above microorganisms in the in vivo or in vitro synthesis of biologically active modified peptides.

The term "modified peptides" refers to analogs of wild type peptides or peptides having novel amino acid sequences.

2. Description of the Background

Peptide synthetases are a group of prokaryotic and eukaryotic enzymes involved the a non-ribosomal synthesis of numerous peptides. Non-ribosomal synthesis is also known as thiotemplate synthesis (Kleinkauf, H. and von Doren, H., (1987), Ann. Rev. Microbiol., 41: 259–289).

These peptides (of which several hundred are known) often have non-linear cyclic structures (cyclosporin, tyrocidin, mycobacillin, surfactin and others) or branched cyclic structures (polymyxin, bacitracin and others) and contain amino acids not usually present in proteins as well as D-amino acids.

Peptide synthetases are multienzymatic complexes consisting of one or more enzymatic subunits. The complexes are characterized by the presence of one or more repeated structural units (super-domains) which contain an activation region (DDA) which recognizes a specific amino acid.

Each DDA catalyzes a series of enzymatic reactions, which eventually links each amino acid into a peptidic chain. The enzymatic reactions include:

1-recognition of the amino acids, 2-activation of the amino acids as amino-acyladenylates,

3-binding of the activated amino acid to the enzyme by the thioester bond between the carboxylic group of the amino acid and the SH group of an enzymatic co-factor which is itself bound to the enzyme inside each DDA, and 4-formation of the peptidic bonds among the amino acids.

In addition, the DDA which couple D-amino acids into the peptidic chain also catalyze the racemization of L-amino acids to D-amino acids.

Finally, the multi-enzymatic complex also contains a conserved domain after the last DDA, whose sequence has homologies with various thioesterases, and in particular contains the consensus sequence of their active sites which terminates coupling and releases the peptide product.

In peptide synthetases there are as many DDAs as amino acids which form the peptide. For example the complex of the surfactin synthetase which catalyzes the polymerization of the lipopeptide having the structure:

consists of three enzymatic subunits of which the first two include three DDAs each, whereas the third has only one DDA. These domains are responsible for the recognition, activation, binding and polymerization of L-Glu, L-Leu, D-Leu, L-Val, L-Asp, D-Leu and L-Leu.

Figure 1:
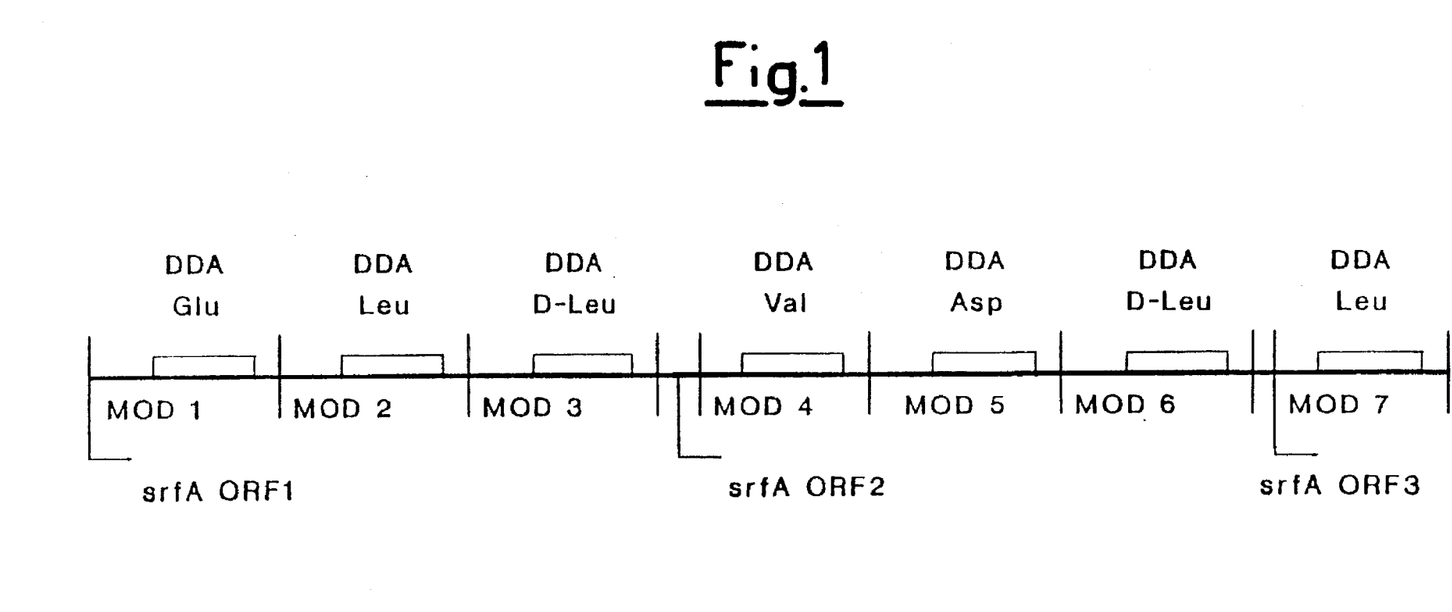
FIG. 1: organization of the DNA coding for the surfactin synthetase wherein the open boxes represent DDA-activation domains MOD-modules which code for the repeated super-domains.

A similar organization in discrete, repeated units (modules) (see FIG. 1) occurs in the genes encoding the synthetases.

The structure with repeated domains of the peptide synthetases is conserved among the bacterial and fungal species, as shown by the sequence characterization data of the operons srfA (Cosmina et al. (1993) Mol. Microbiol. 8, 821–831), grsA and grsB (Kratzxchmar et al. (1989) J. Bacterial. 171, 5422–5429) tycA and tycB (Weckermann et al. (1988) Nucl. Acid. Res. 16, 11841–11843) and ACV from various fungal species (Smith et al. (1990) EMBO J. 9, 741–747; Smith et al. (1990) EMBO J. 9, 2743–2750; MacCabe et al. (1991) J. Biol. Chem. 266, 12646–12654; Coque et al. (1991) Mol. Microbiol. 5, 1125–1133; Diez et al. (1990) J. Biol. Chem. 265, 16358–16365). Inside the activation domains even of distant species there are sequences with high homology, some of which are conserved and specific for all the peptide synthetases. Other regions, inside the DDA, are more conserved among the DDA which recognize the same amino acid (Cosmina et al. (1992) Mol. Microbiol. 8, 821–831).

The sequence of the peptide produced is determined, at the gene level and therefore at the enzyme level, by the order and sequence characteristics of the single activation domains. This is consequently a basic characteristic of the thiotemplate synthesis system.

It is known that many of the peptides synthesized by the non-ribosomal method have antibiotic, antifungal and immunosuppressive properties and are therefore of considerable commercial importance.

As a result many laboratories are continually looking for molecules with improved properties with respect to the known ones (for example molecules which have immunosuppressive activities similar to those of Cyclosporin A but with less toxicity) or with new activities.

The preparation of new peptide molecules can be carried out using known technology such as by: 1) selecting new host microorganisms, 2) mutagenizing peptide-producing organisms with chemical agents and selecting the mutants which produce a modified peptide, and 3) changing the growth substrates of the peptide-producing organisms to try and favor the incorporation of different amino acids into the peptides.

These methods require a great amount of time, are have a high degree of uncertainty as to the probability of obtaining new molecules and, in addition, offer very few possibilities of directing the design of new peptides.

Another method suggested by existing technology relates to the chemical synthesis of the desired peptides.

The disadvantage of this technology lies in the difficulty of the synthesis, especially for syntheses an a large scale, and above all when the synthesis concerns complex molecules (cyclic, branched structures containing a high number of amino acids or modified amino acids).

SUMMARY OF THE INVENTION

The object of the present invention is to overcome the disadvantages of the known art mentioned above.

In particular it has been found that it is possible, through techniques of genetic manipulation, to substitute the order or nature of various domains which form a particular peptide synthetase without changing the functionality of the synthetase itself.

In addition to this the modified synthetase is capable of completing the synthesis of the peptide which will be modified in its sequence according to the modification created on the enzyme.

For example, if a synthetase consists of structural domains a, b and c which catalyze the synthesis of peptide A-B-C-, the present invention shows us that it is possible to create an enzyme a+b, a+c or b+c, catalyzing formation of, respectively, peptides A-B, A-C and B-C. It is similarly possible to create new enzymes by combining these structural domains in new way (eg. a+a+b, a+b+c+d, etc.), which catalyze formation of peptides whose sequence is determined by the specificity of each domain.

In accordance again with the present invention domain a, with specificity for amino acid A, can assume specificity for amino acid B, by modifying part of the DDA sequence of the domain itself.

At this point it is important to remember again that the domain structure of the synthetase is conserved among different species and that the domains of the various species shows a high degree of homology.

According to a preferred embodiment of the present invention hybrid synthetases can be created in which here can be a combination of domains also deriving from synthetases of phylogenetically separated organisms.

This consequently enables the in vivo or in vitro preparation of analogous peptides of interest or of peptides having new sequences by the creation of new peptide synthetases which can synthesize peptides having a different sequence from the original one.

In accordance with this, the first aspect of the present invention relates to a method for the biological synthesis of biologically active modified peptides by means of the genetic manipulation of the peptide synthetases.

The present invention also relates to the construction of engineered microorganisms capable of expressing peptide synthetases with a modified specificity of substrate.

A further aspect of the present invention relates to the use of said microorganisms or peptide synthetases extracted from the above microorganisms for the in vivo or in vitro synthesis of biologically active modified peptides.

Further objects of the present invention are evident from the description and examples which follow.

BRIEF DESCRIPTION OF THE DRAWINGS

To provide a better definition of the present invention reference is made to the following figures.

DETAILED DESCRIPTION OF THE PREFERRED EMBODIMENTS

The synthesis method of the present invention includes:
(a) isolating from the chromosomal DNA of strains producing peptide synthetases involved in the synthesis of peptides of interest, at least one region of genes of the peptide synthetases which includes the nucleotide sequence which codes for the activation domain of an amino acid of said peptide;

(b) modifying the sequence of said region by the substitution, deletion or duplication of the nucleotide sequence which codes for said activation domain or part of this;

(c) cloning said modified region in a vector;

(d) transforming a host microorganism with the vector including the modified DNA region;

(e) isolating the transformants capable of expressing the peptide synthetases with a modified specificity of substrate; and finally (f) cultivating the transformed microorganism under suitable conditions for obtaining the desired peptide.

The modification strategies of the synthetases can vary according to whether there is a requirement for 1) a deletion of a domain or part of this, 2) a substitution of domains or part of these, 3) an addition of one or more domains, 4 additions, substitutions and deletions of domains or part of domains at the 5' end of the DNA coding for the synthetase and additions, substitutions, and deletions of domains or parts of domains at the 3' end of the DNA coding for the synthetase.

Four of the procedures which can be used to create these modifications are illustrated below.

1) Deletion of domains or portions of domains

Figure 2:
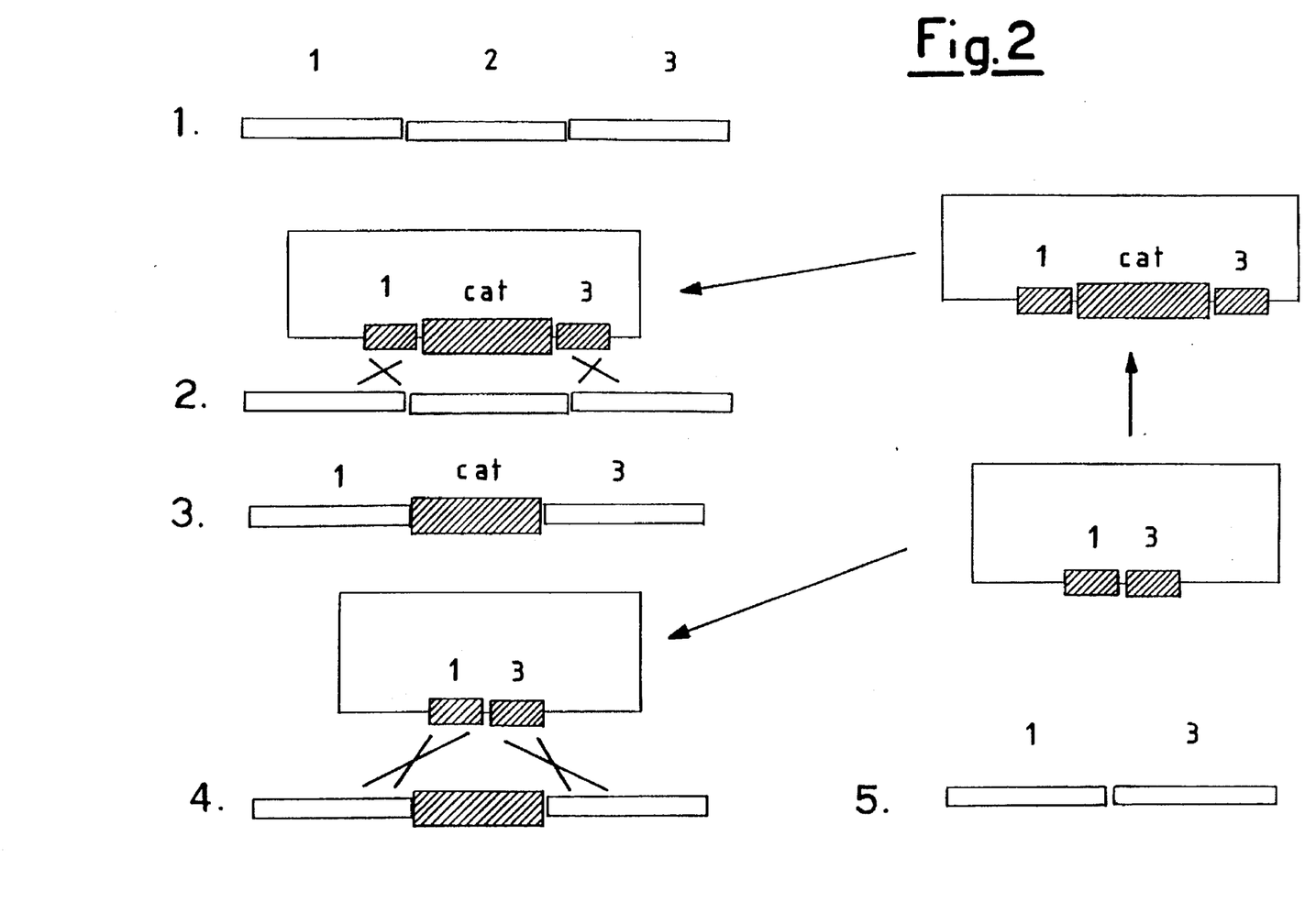
FIG. 2: scheme of the method for the deletion of domains

FIG. 2 schematically illustrates the strategy proposed which is initially based on:

a) Preparation of a plasmid which carries a genetic marker (eg. resistance to an antibiotic) in the position between the DNA coding for the carboxy-terminal region of the domain which precedes the one to be removed and the DNA coding for the N-terminal region of the domain which follows.

b) Transformation of the wild type strain with the plasmid at point 1, selection for the resistance to the marker, and isolation of the clone in which, owing to double crossing-over, the genetic marker is substituted for the domain to be removed.

c) Construction of a plasmid in which the regions coding for the carboxy-terminal end of the domain which precedes the one to be removed and for the N-terminal end of the domain which follows are adjacent.

d) Transformation of the clone isolated in point b) with the plasmid described in point c) and selection of the clone which has lost the antibiotic-resistance marker.

2) Substitution of domains or part of domains

Figure 3:
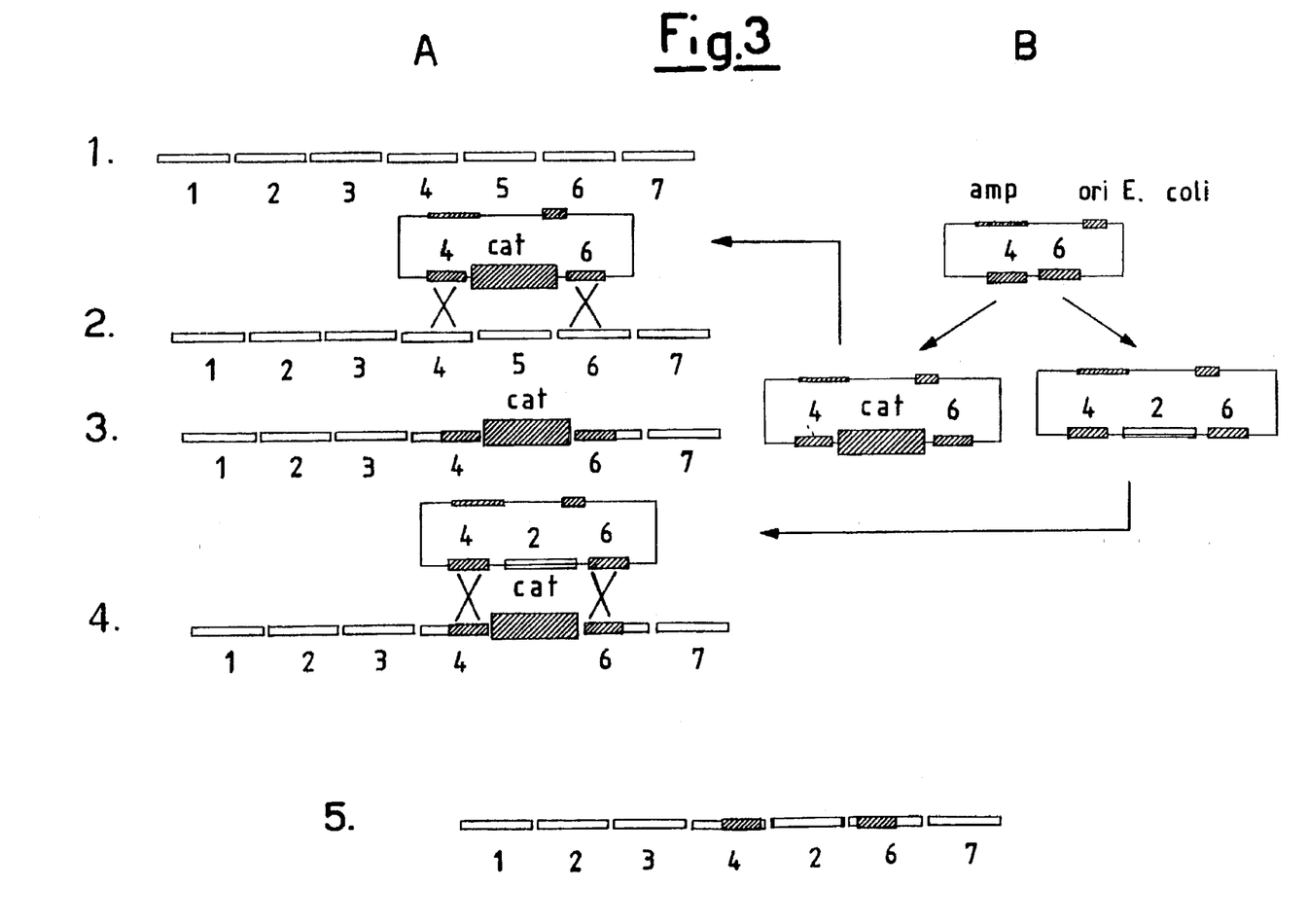
FIG. 3: scheme of the method for the substitution of domains

FIG. 3 schematically illustrates the proposed strategy which is initially based on:

a) and b) Preparation of a plasmid and transformation of the wild type strain as shown in steps a) and b) of point 1 above.

c) Isolation of a structural domain (or part of this) starting from the chromosomal DNA (or MRNA messenger) extracted from a producer organism. Three isolation techniques can be used (i) cutting the chromosomal DNA with restriction enzymes and isolating a fragment coding for the domain of interest after its identification by means of Southern blot, (ii) isolation of the domain of interest by genetic amplification (PCR) using suitable primers, when the sequence of the domain is known, (iii) genetic amplification (PCR) with degenerated primers which correspond to the sequences highly conserved on the DDA. Sequencing and characterization of the amplified fragments as well as cloning of the DDA of interest can be performed according to conventional techniques.

d) Construction of a plasmid as in point a) but wherein he DNA coding for the resistance marker is substituted y the domain isolated in point c).

e) Transformation of the strain isolated in point with the plasmid described in point d) and isolation of the clone in which the resistance marker has been substituted with the domain present on the transforming plasmid by recombination.

3) Addition of domains

Figure 4:
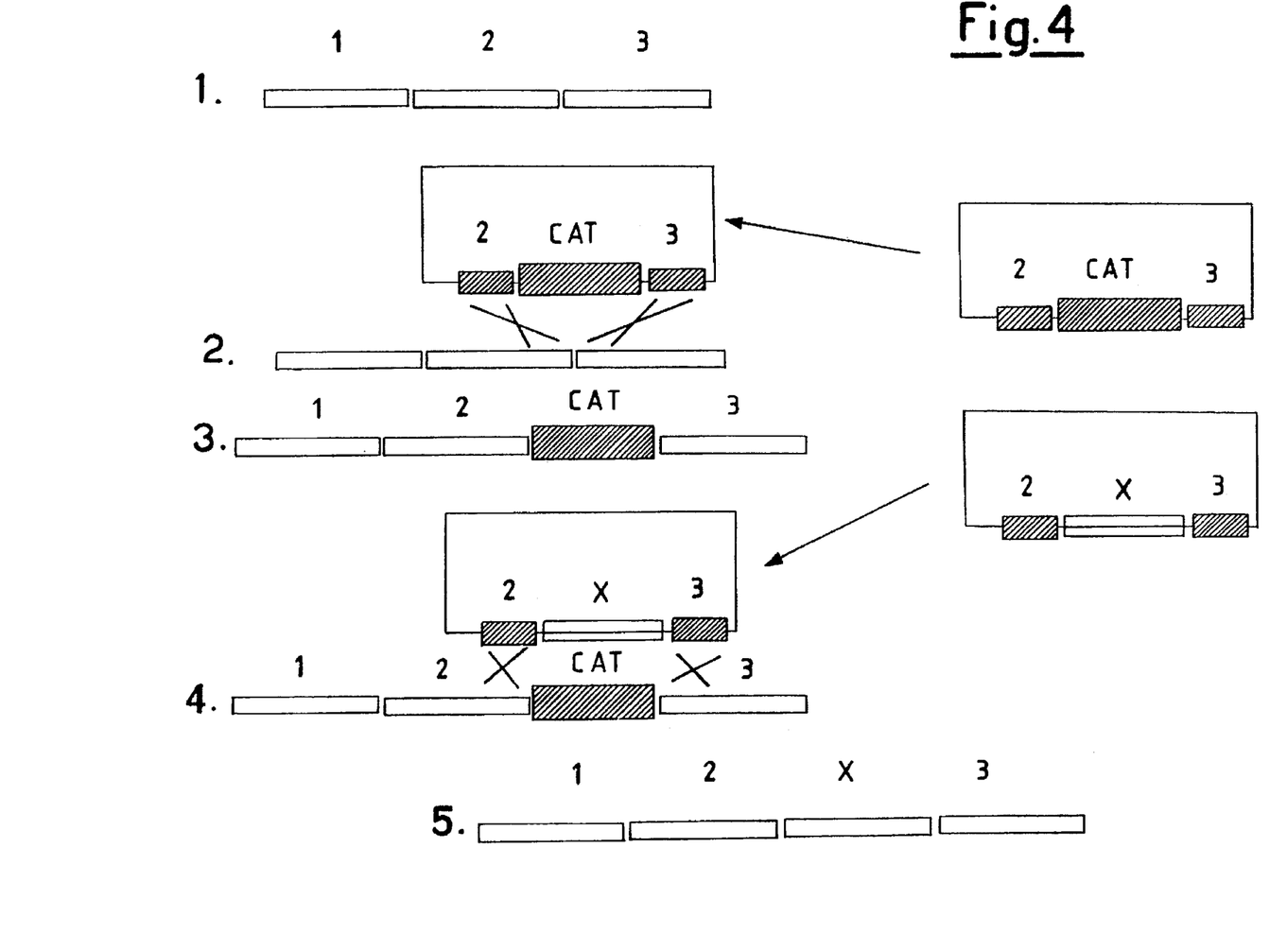
FIG. 4: scheme of the method for the addition of domains

FIG. 4 schematically illustrates the strategy and is based on:

a) Construction of a plasmid which carries a genetic marker in the intermediate position between the DNA coding for the carboxy-terminal region and the N-terminal region of two contiguous domains between which the new structural domain must be inserted.

b) Transformation of the wild-type strain with the plasmid of point a), selecting for the resistance to the marker and isolation of the clone in which, owing to double crossing-over, the genetic marker has become integrated among the domains which must respectively precede and follow the new domain to be added.

c) Isolation of the domain to be added to the synthetase as described in point c) of the previous example.

d) Construction of a plasmid as in point b) but in which the genetic marker is substituted with the DNA coding for the domain isolated as in point c) of example 2.

e) Transformation of the clone isolated in point b) with the plasmid constructed as in point d) and isolation of a new clone in which the genetic marker has been lost owing to its substitution, by double crossing-over, with the new domain situated on the transforming plasmid.

4) Additions, substitutions and deletions of domains in position 5' of the DNA coding for the synthetase.

Figure 5:
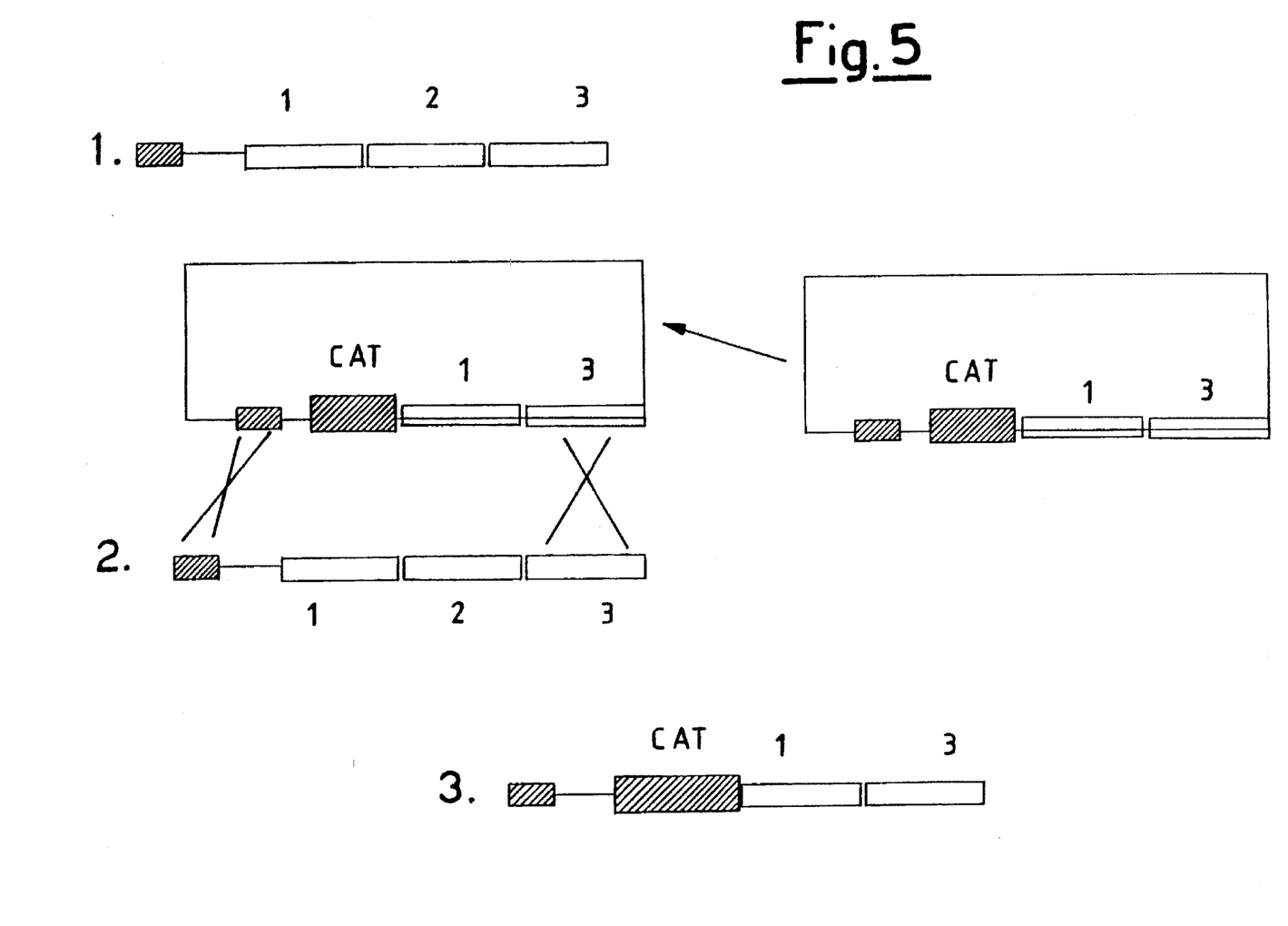
FIG. 5: scheme of addition, substitution or deletion of domains in position 5' of the DNA coding for the synthetase

FIG. 5 schematically illustrates the strategy used and is based on:

a) Construction of a plasmid in which the DNA coding or an antibiotic resistance marker is preceded by a NA region situated upstream from synthetase gene and followed by portion 5' of the gene. This portion codes or one or more domains.

b) Modification of the plasmid in point a) using known techniques of plasmid manipulation in order to remove, substitute or add domains inside region 5' coded by the synthetase gene.

c) Transformation of the wild-type strain with the modified plasmid obtained as described in point b) electing for the resistance to the antibiotic coded by he plasmid.

d) Isolation of the clone in which, owing to double crossing-over, modified region 5' of the synthetase ene present on the plasmid has substituted the corresponding region of the wild-type strain.

5) Additions, substitutions and deletions of domains in position 3' of the DNA coding for the synthetase.

a) Construction of a plasmid in which the DNA coding for an antibiotic resistance marker is followed by a region situated downstream the synthetase gene and receded by coding portion 3' of the gene itself. This portion codes for one or more domains of the synthetase.

b) Modification of the plasmid in point a) using known techniques of plasmidic manipulation in order to remove, substitute or add domains inside coding region of the synthetase gene.

c) Transformation of the wild-type strain with the modified plasmid obtained in point b) selecting for the resistance to the antibiotic coded by the plasmid isolation of the clone in which, owing to double crossing-over, modified region 3' of the synthetase gene present on the plasmid has substituted the corresponding region of the wild-type strain.

The strategy examples described above illustrate the necessity of having suitable host organisms containing the synthetase to be modified and vectors suitable for manipulation.

Examples of vectors suitable for the purposes of the present invention can be selected from expression integration plasmids. The latter are plasmids which are not capable of being autonomously replicated in the host microorganism but which can be integrated in their chromosome by means of a Campbell-type recombination (Vosman, B. et al. (1986) Mol. Gen. Genet. 204, 524–531). The recombination occurs among sequences of homologous DNA present on the plasmid and chromosome. To show that the recombination has occurred, the plasmid must contain a selectable marker in the host train. Integration plasmids can be selected for example from pJM103 and pJM102 which contain the cat gene (chloramphenicol acetyltransferase) as a marker gene which gives resistance to the antibiotic chloramphenicol.

Host microorganisms suitable for the purpose of the present invention can be selected from bacteria, yeast or fungi which produce peptide synthetases.

Said microorganisms can be selected from those which produce the natural peptide which is to be modified or can belong to different genera. The transformation of these microorganisms with the vector containing the modified DNA region and the selection of the transformants can be carried out with conventional techniques (Maniatis et al. (1982) Molecular Cloning—A Laboratory Manual—Cold Spring Harbor Laboratory ed. New York).

The microorganisms thus selected can be cultivated under suitable conditions and the modified peptides produced can be recovered and purified using conventional techniques.

As an alternative, the peptide synthetases expressed by said microorganisms can be isolated and purified and used for the in vitro synthesis of the modified peptides. The peptide synthetases can be used in solution as such or immobilized on insoluble supports to allow their continual use.

Finally, the method of the present invention enables:

1- the production of strains which produce modified peptides and enzymatic complexes which synthesize these, thus avoiding processes of chemical synthesis or manipulation of the in vitro reaction conditions by natural purified enzymes;

2- the availability of a variety of unusual and modified substrates inserted in the synthesized natural antibiotic peptides by the non-ribosomal method which can be used for the synthesis of analogous peptides;

3- the production of microorganisms which are different from those which naturally produce the peptide of interest, inserting the appropriate activation domains into synthetase genes well-characterized in the host species selected from those which are easily accessible for genetic manipulation.

EXAMPLES

The following examples provide a better illustration of the present invention and should not be read to restrict it in any way.

Example 1

Figure 6:
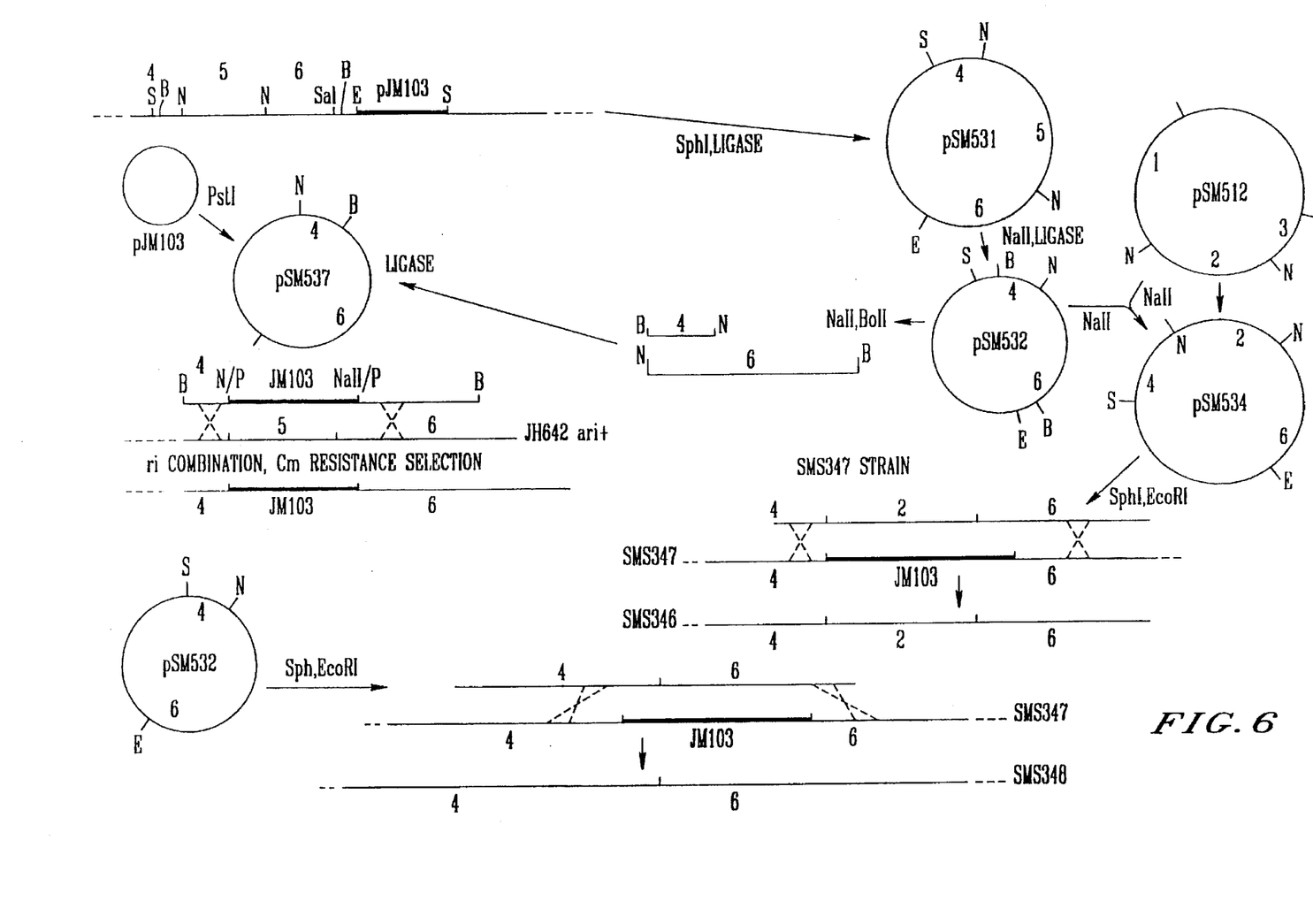
FIG. 6: construction of strains SMS346 and SMS348

Construction of the strain *B.subtilis* SMS346 (FIG. 6)

The region which codes for the activation domain of the fifth amino acid (Asp) of surfactin, has been substituted with the activation domain of the second amino acid (Leu). The initial step involved the isolation on plasmids of the chromosomal region including the sequences which code for activation domains 4, 5 and 6 of the surfactin synthetase.

Construction of the plasmid pSM532

The fragment SaII-EcoRI of 8 kb, which includes part of activation domain 6, was isolated from the clone SRF lambda 5 ATCC75060.

Subsequently the fragment (1 µg) was ligated in a ligation mixture with integration plasmid pJM103 (M. Perego and J. Hoch (1991), J. Bacteriol. 173:25142520), (200 ng), linearized with restriction enzymes SaiI and EcoRI. The resulting ligation mixture, containing 1 unit of the enzyme T4-DNA ligase, was incubated for 16 hours at 14° C.

An aliquot of the above mixture was then used to transform 100 µl of competent cells of *B. subtilis* JH642 srf⁺ (producers of surfactin). The transformants were selected on Shaeffer sporulation medium to which 5 µg/ml of chloramphenicol had been added.

Analysis of the clones resistant to chloramphenicol ($Cm^R$) revealed the insertion of pJM103 by Campbell type recombination with single crossing over downstream the EcoRI site of domain 6. Ten $Cm^R$ colonies were inoculated in LB medium and the chromosomal DNA was extracted from the cultures.

This chromosomal DNA (5 µg) was digested with SphI, which cuts in the domain 4, and subjected to ligase reaction under conditions which favor the circularization (concentration of the DNA<1 ng/ml). The ligase products were used to transform competent cells of *E.coli* JM109 (BRL) and the transformants were selected on LB medium to which Ampicillin (100 µg/ml) had been added. Plasmid pSM531 consisting of plasmid pJM103 and a fragment SphI-EcoRI which includes the sequence of 2000 bp of domain 4, sequence 3200 bp of domain 5 and sequence 3700 bp of domain 6, was isolated from one of the clones resistant to ampicillin ($Amp^R$).

Plasmid pSM531 (2 µg) was digested with 2 units of restriction enzyme NsiI (BRL) whose cutting sites are situated exactly between one domain and another. The ligation of the fragment with greater dimensions (consisting of domains 4 and 6 and vector pJM103) created plasmid pSM532 in which the 3' end of domain 4 becomes adjacent to 5' end of domain 6.

B) Construction of plasmid PSM537

The object of the experiment was to construct a plasmid in which the sequence of pJM103 was inserted between the 3' end of domain 4 and 5' end of domain 6.

Plasmid pSM532 (20 µg) was digested with 20 units of the enzymes BclI and NsiI. Bands of DNA corresponding to the following fragments were isolated from the digestion mixture by elution from agarose gel at 0.6%:

BclI-NsiII of 900 bp (domain 4) and
NsiI-BclI of 3700 bp (domain 6).

The two fragments were subsequently ligated in a ligation mixture with integration plasmid pJM103 previously linearized with restriction enzyme PstI. The resulting ligation mixture, containing equimolar quantities of the three fragments and 1 unit of T4-DNA ligase enzyme, was incubated for 16 hours at 14° C.

An aliquot of said mixture was used to transform 100 µl of competent cells of *E.coli* JM109 (BRL) ampicillin sensitive, the transformants being selected on LB medium containing Ampicillin (100 µg/ml).

Plasmid pSM537 in which the portion of the pJM103 vector is flanked by domains 4 and 6 in the correct direction, was isolated from one of the $Amp^R$ clones, according to the rapid extraction method described by Holmes and Quigley (1981) Anal. Biochem., 114: 193–197).

C) Construction of plasmid PSM534

Before isolating the fragment of chromosomal DNA which codes for domain 2 of the surfactin synthetase, it was necessary to introduce into plasmid pSM512 (ATCC 68634), by site-specific mutagenesis, the NsiI restriction site upstream from the region coding for activation domain 2 of surfactin synthetase at 3547 nucleotide of srfa.

The DNA fragment NsiI-NsiI of 3200 bp corresponding to domain 2 was subsequently isolated from the mutagenized plasmid pSM512. Equimolar quantities of this fragment and plasmid pSM532 linearized with restriction enzyme NsiI were ligated in a ligation mixture at 14° C. for 16 hours and the resulting mixture was used to transform competent cells of *E. coli* JM109. Analysis of the transformants selected on medium containing ampicillin revealed a clone containing a plasmid, called pSM534, consisting of plasmid JM103 and activation domains 4, 2 and 6.

D) Construction of the strain *B.subtilis*SMS347

Competent cells of *B. subtilis* JH642srf⁺ were transformed with plasmid pSM537 linearized with restriction enzyme BclI. The transformants were selected an plates of sporulation medium containing chloramphenicol 5 µg/ml. Thirty-six colonies ($Cm^R$) were inoculated in LB medium and the chromosomal DNA was extracted from the cultures. To verify the integration and type of recombination which had taken place, the chromosomal DNA was amplified by (PCR) using the following oligonucleotides:

5' GCA GCG ATT ATG AAG GAC CGC TCA GTA GAA AC 3' (Sph) (SEQ ID NO: 1)

5' CAT ATG TTT CGC TCC CGC CTT CTG TAA TTC 3' (M6N) (SEQ ID NO: 2)

5' TCT GAT CGA CCG CGA GTA TGG CGG CTC TAT 3' (M4F) (SEQ ID NO: 3)

The distance on the chromosome between two sequences in domains 4 and 6 must prove to have increased by about 600 bp when domain 5 is substituted by the sequence of pJM103 by double crossing-over recombination occurring on the one side between 900 bp BclI-NsiI of pSM537 with domain 4 of the chromosome, and on the other side between 3700 bp NsiI-BclI of pSM357 with domain 6 also situated on the chromosome.

Three of the 36 clones analyzed showed amplification products of the required dimensions. One of the clones positive to this screening is called SMS347.

E) Construction of the strain *B.subtilis* SMS346

To substitute the sequence of pJM103 on the chromosome of *B.subtilis* SMS347 with domain 2 the following procedure was carried out.

Plasmid pSM534(5 µg) was digested with the restriction enzymes EcoRI and SphI and a fragment of DNA containing part of domain 4, domain 2 and part of domain 6 was isolated from the digestion mixture. This fragment was inserted into plasmid pSM143 (ATCC 53038) containing the gene coding for resistance to kanamycin used to transform competent cells of *B. subtilis* SMS347. The ratio between the quantity of linear DNA and plasmid is 10:1. The recombinant colonies, obtained from four transformation experiments, selected an LB plates containing kanamycin, were tested to evaluate which of these had lost resistance to chloramphenicol (i.e. the sequence of plasmid JM103).

Among the 1200 thus tested, 5 proved to be sensitive to the antibiotic. Their chromosomal DNA was analyzed using the PCR technique to verify both the loss of pJM103 sequences and the acquisition of domain 2 between domains 4 and 6.

For this purpose cross checks were carried out on both the chromosomal DNAs being tested and on the reference DNA isolated from *B. subtilis* JH642 srf⁺ using the following oligonucleotides:

5' GCA GCG ATT ATG AAG GAC CGC TCA GTA GAA AC 3' (Sph) (SEQ ID NO: 1)

5' CAT ATG TTT CGC TCC CGC CTT CTG TAA TTC 3' (M6N) (SEQ ID NO: 2)

5' TCT GAT CGA CCG CGA GTA TGG CGG CTC TAT 3' (M4F) (SEQ ID NO: 3)

Two colonies proved to have the required characteristics, i.e. a chromosomal structure of the type of domains 1-2-3-4-2-6-7, also due in this case to a double crossing-over event between the homologous regions of domains 4 and 6 present on plasmid pSM534 and on the chromosome. One of these colonies was called SMS345.

*B-subtilis* SMS345 was grown in liquid medium without selective pressure produced by kanamycin. After suitable dilutions it was observed that the strain was no longer able to grow in the presence of the above antibiotic as it had lost the pSM143 which gave it this resistance. This resulting strain, which however maintained the required characteristics in its chromosomal DNA, took the name *B.subtilis* SMS346.

Example 2

Construction of the strain *B.subtilis* SMS348 (FIG. 6)

Plasmid pSM532 (5 μg) was digested with the restriction enzymes EcoRI and SphI and a fragment of DNA containing part of domains 4 and 6 was isolated from the digestion mixture. This fragment was inserted into plasmid pSM143 and to transform competent cells of *B-subtilis* SMS347. The ratio between the quantity of linear DNA and plasmid is 10:1. The recombinant colonies, obtained from four transformation experiments, selected on plates containing kanamycin, were tested to evaluate which of these had lost resistance to chloramphenicol (i.e. plasmid JM103). Among the 1800 thus tested, 80 proved to be sensitive to the antibiotic chloramphenicol.

Analysis by means of PCR of the chromosomal DNA extracted from these colonies showed a clone with the required characteristics: (i) loss of the pJM103 between domains 4 and 6 of the chromosome and (ii) correct adjacent position in the NsiI site of the above domains. This clone has been called SMS348.

Example 3

Figure 7:
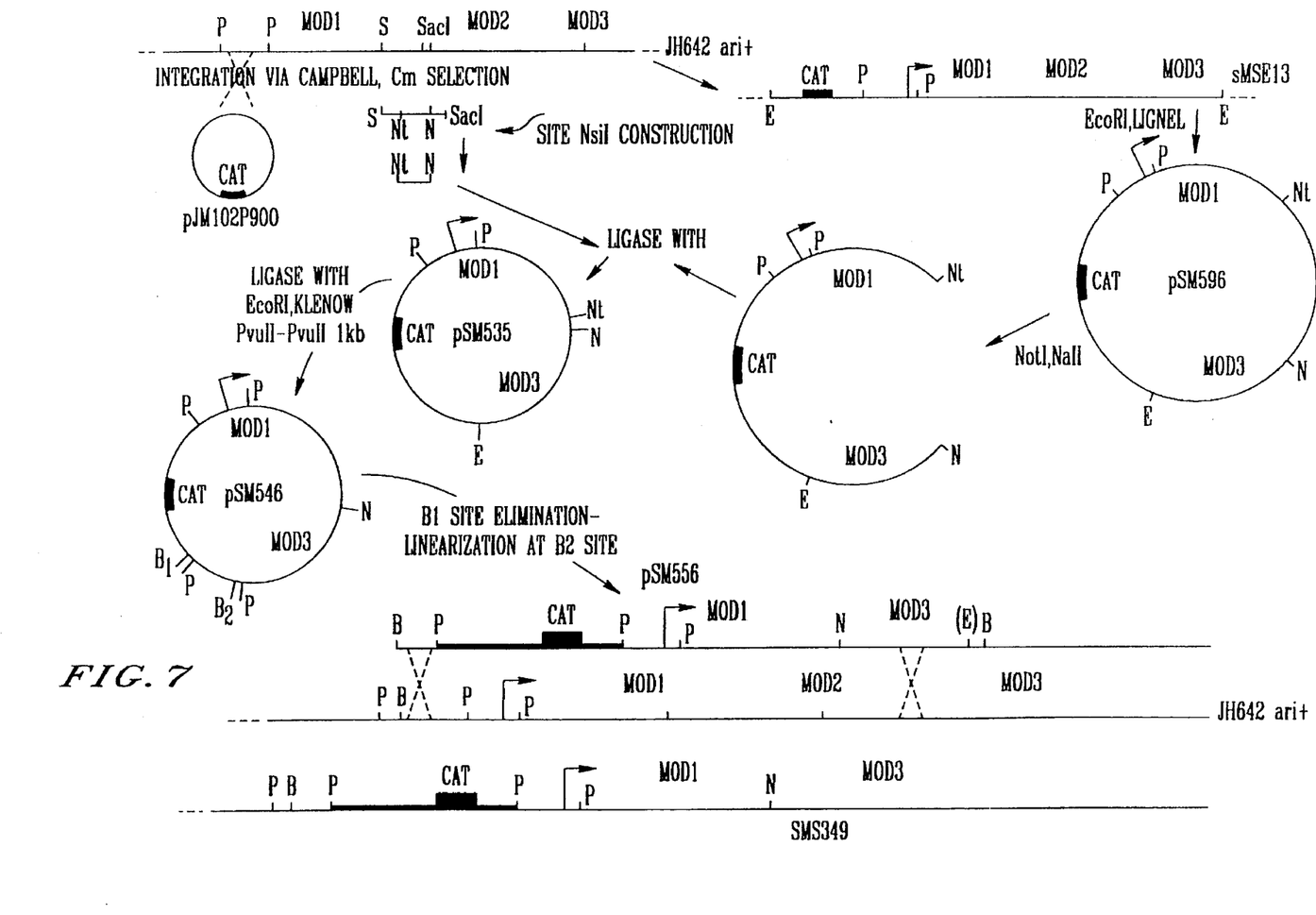
FIG. 7: construction of strain SMS349

Construction of the strain *B.subtilis* SMS349. (FIG. 7)

To obtain the deletion of the second activation domain of the surfactin synthetase the plasmid pSM536 as used; said plasmid being formed in linear sequence from fragment PvuII—PvuII of approximately 900 bases upstream the promoter srfA, a fragment containing the genetic marker CAT, the srfA promoter followed by the region of the operon which codes for the first sub-unit of the surfactin synthetase up to base 3547 in which a NsiI site has been inserted for mutagenesis, and domain three contained in the region NsiI6664-EcoRI9230 of operon srfA. Then, in this plasmid the domain one and three are exactly adjacent to each other in the NsiI site.

Plasmid pSM536 was obtained according to the steps described below.

A) Construction of the strain SMSE13

1 μg of the plasmid pSRF1 ATCC 68632, containing the promoter of operon srfA, was digested with 5 units of the restriction enzyme PvuII (BRL). The fragment PvuII—PvuII of about 900 bp subsequently ligated in ligation mixture to integration plasmid pJ102 linearized with PvuII, was isolated from the digestion mixture.

Competent cells of *E.coli* pJM109 transformed with this mixture were selected on LB plates containing 100 μg/ml of Ampicillin. The plasmid called pJM102-P900 consisting of integration pJM102 and fragment PvuII—PvuII, was isolated from one of the clones resistant to Ampicillin.

1 μg of this plasmid was used to transform competent cells of *B. subtilis* JH642 srf⁺. One of the clones resistant to chloramphenicol (CMR), which had integrated pJM102 on the chromosome was called SMSE13.

In this strain the DNA corresponding to pJM102 is inserted on the chromosome upstream of the fragment PvuII—PvuII of 900 bp which includes the initial codon of operon srfA. The direction of this plasmid DNA with respect to operon srfA is such that the site EcoRI of the Multi Cloning Site of pJM102 is situated at the end of pJM102 opposite operon srfA.

B) Construction of plasmid DSM596

The chromosomal DNA (1 μg) of strain SMSE13 was digested with 2 units of EcoRI and then ligated at low concentrations (1 ng/ml) to favour the circularization of the fragments resulting from the digestion.

An aliquot of ligation mixture was used to transform competent cells of *E.coli* JM109. Plasmid pSM596 comprising the DNA of pJM102 and a chromosomal fragment of about 10 kilobases consisting of promoter srfA and the first 9230 bases of the ORF1 of srfA which includes modules 1, 2 and 3, was isolated from an Amp$^R$ clone.

C) Construction of plasmid pSM536

Plasmid pSM596 was digested with the enzymes SacI nd SaI and the fragment of 850 bp containing the unique site NotI at the 31 end of module 1 was isolated and cloned in vector RFmp18 (New England Biolabs). The site NsiI was then introduced into this vector according to the known techniques of mutagenesis using the synthetic oligonucleotide 5 'TTT GAG ATG CAT CAT TTG ATT TCT GAC 3' (SEQ ID NO 4).

The resulting vector RFmp18-NsiI (30 μg) was digested with 30 units of the enzymes NotI and NsiI and the obtained fragment NotI-NsiI of 125 bp was ligated with the fragment NotI-NsiI of 11 Kb resulting from the digestion of pSM596 with restriction enzymes NotI and NsiI. The ligation mixture was used to transform competent cells of *E.coli* JM109. Plasmid pSM536 containing the portion of srfA up to site EcoRI from which module 2 of about 3200 bp was deleted, was isolated from one of the Ampicillin-resistant clones.

D) Construction of plasmid DSM556

To obtain the deletion of module 2 on the chromosome by double crossing-over and selection on chloramphenicol it was necessary to introduce into plasmid pSM536 a fragment of chromosomal derivation situated upstream the promoter of operon srfA and the sequence contained in pSM536. For this purpose the fragment PvuII—PvuII of 1000 bp which maps in a position adjacent to 5' of the fragment PvuII—PvuII of 900 bp used for the construction of SMSE13 and pSM596, as isolated from plasmid pSRF1 (ATCC 68632).

This fragment was ligated with plasmid pSM536 previously digested with EcoRI and protruding ends generated by said digestion were made blunt by treatment with the fragment Klenow of the polymerase I DNA of *E.coli*.

The ligase mixture was used to transform competent cells of *E-coli* JM*109*. The plasmid called pSM546 in which the fragment PvuII—pvuII of 1000 bp was inserted in the site EcoRI in the right direction, was isolated from one of the Ampicillin-resistant clones. The site BamHI, outside the fragment PvuII—pvuII of 1000 bp, was then eliminated by partial digestion (1 hour at 37° C.) of 1 μg of pSM546 with 0.1 U of enzyme, subsequent reaction with the fragment Klenow of polI to obtain blunt ends and recircularization by ligase.

The resulting plasmid after circularization was called pSM556.

E) Construction of strain SMS349

To obtain the deletion of module two on the chromosome, the strain producing surfactin JH642 srf$^+$ was transformed with pSM556 linearized with BamHI to favor recombination with double crossing-over between the chromosome and the plasmid.

Out of 20000 colonies which had acquired resistance to chloramphenicol, 10% had lost the halo (index of surfactin production), whereas 90% had maintained it. The chromosomal DNA was extracted from 24 halo colonies and analyzed by gene amplification reactions (PCR) with the following oligonucleotides:

(M1F) 5' ACA GCA CGC CGA GAC AGA AAA TTC ACG 3' (SEQ ID NO: 5)

(M24) 5' CAA CCG TTT GCA AAG CTT TTC TG 3' (SEQ ID NO: 6)

(M3R) 5' TGC GCA GAG CAT CAG CTT TGC CTG CTT CT 3' (SEQ ID NO: 7)

(M1vs3) 5' ACA GCA CGC CGA GAC AGA AAA TTC ACG 3' (SEQ ID NO: 8)

(M3vs1) 5' AGC TCC TTC AGC CAA TGC TCT TCT TGC 3' (SEQ ID NO: 9)

(M2Rev) 5' CGC CTT CTC TGG ATC AGC CGC AGC ATC TTC 3' (SEQ ID NO: 10)

The analysis showed that deletion on the chromosome of module 2 had occurred in two colonies.

One of these colonies was called B. subtilis SMS349.

Example 4

Functional analysis of recombinant strains.

A) Purification of the enzymatic subunit of surfactin synthetase srfAORF2 (4-2-6).

A colony of the strain B. subtilis SMS346 grown on a plate of maximum sporulation medium was inoculated in 21 of LB medium and incubated at 37° C. for 16 hours. The culture was centrifuged at 5,000 rpm for 20 minutes and the cells (13.8 g humid weight) were resuspended in 30 ml of buffer B (50 mM Tris Hcl, pH 7.8, 5 mMDTE, 0.25 mM EDTA, 10% w/v sucrose) to which PMSF (1 mM), 1 mg/ml of lysozyme and 20 mg of DNAse I and ribonuclease (Boheringer) had been added. The suspension was incubated at 30° C. for 1 hour. The cellular lysis was then completed using a French Press at a working pressure of 12000 psi.

After centrifugation at 30,000 rpm for 30 minutes, the supernatant was brought to a 70% saturation with ammonium sulphate to precipitate the proteins. The precipitate was separated by centrifugation at 30,000 rpm for 30 minutes and then resuspended in 20 ml of buffer 20 mM Tris-HCl pH 7.5 containing 1 mM PMSF (phenyl methane sulphonyl fluoride). The resulting solution was dialyzed for 16 hours against the same buffer and then charged into a Q Sepharose FF column (2.6×12 cm) (Pharmacia) equilibrated with 20 mM Tris-HCl, pH 7.5 and eluted with the same buffer at a flow of 1.5 ml/minute.

The proteins were eluted with a gradient of NaCl from 0 to 1M in 20 mM Tris-HCl, pH 7.5. The fractions containing the enzymatic subunits of surfactin synthetase srfAORF1 and srfAORF2 (4-2-6), identified by electrophoresis on SDS-PAGE (Laemmli, Nature, 227, 680685, 1970), were collected, concentrated at 9.5 ml and then charged into a Sephacryl® S-300 HR column (Pharmacia) at a flow of 0.33 ml/minute.

After elution, the fractions containing srfAORF1 and srfAORF2 (4-2-6) were collected (13.3 mg of total proteins), analyzed on SDS-PAGE and, after transferring onto a nitrocellulose membrane 2 μm, were tested by western-Blot using anti-srfAORF1 and anti-srfAORF2 antibodies. Both antibodies recognize the band of about 400 KD, confirming the presence of both srfAORF1 and srfAORF2 (4-2-6) in the purified protein preparation (point c).

This preparation was used for the enzymatic tests described below.

B) Purification of srfAORF2 (4-6)

The same procedure described in step A) was carried out starting from 11 g of cells of strain B.subtilis SMS348. After precipitation with ammonium sulphate at 70% of saturation, the proteins were resuspended in 12 ml of buffer B and charged onto a Q Sepharose FF column (2.6×12 cm) at a flow of 0.3 ml/minute.

The fractions containing srfAORF2 (4-6), identified by electrophoresis on SDS-PAGE, were collected and charged onto a Sephacryl® S-300 HR column at a flow of 0.33 ml/minute.

The fractions containing srfAORF2 (4-6) were collected and analyzed on SDS-PAGE and then used in the enzymatic tests described below.

C. Analysis of the enzymatic activity.

The enzymatic activity of the modified proteins was tested by directly measuring the bond of the radioactive amino acid to the purified enzyme as described by Ullrich et al. (1991) Biochemistry 30: 6503–6508.

Figure 8A:
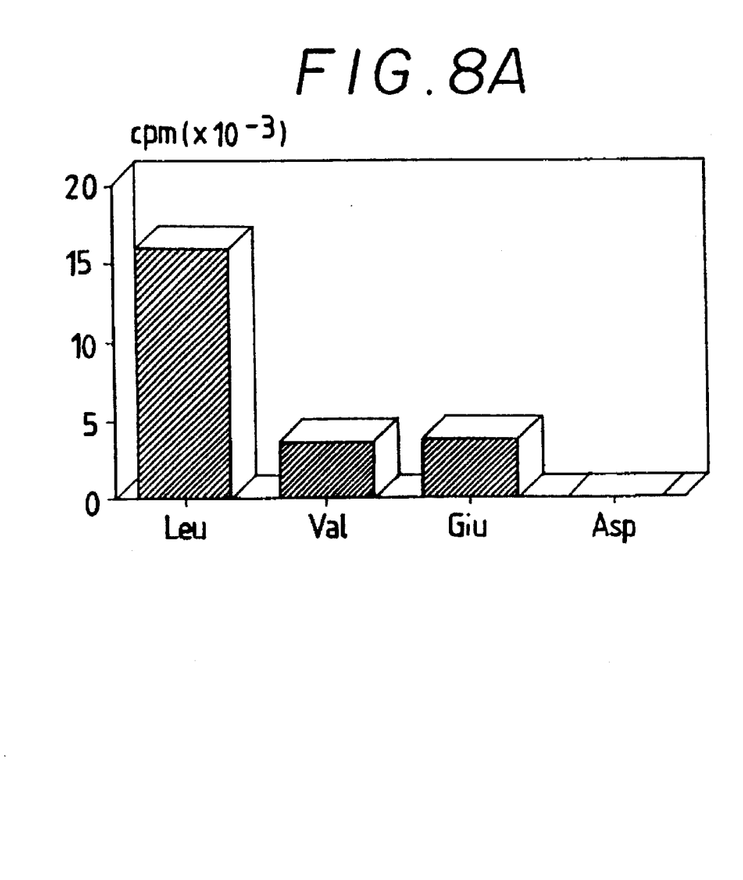
FIG. 8: bond activity of the amino acids of the preparation containing subunits srfAORF1 and srfAORF2 (4-2-6) (A) and bond activity of the amino acids of the preparation of srfAORF2 (4-6) (B).
Figure 8B:
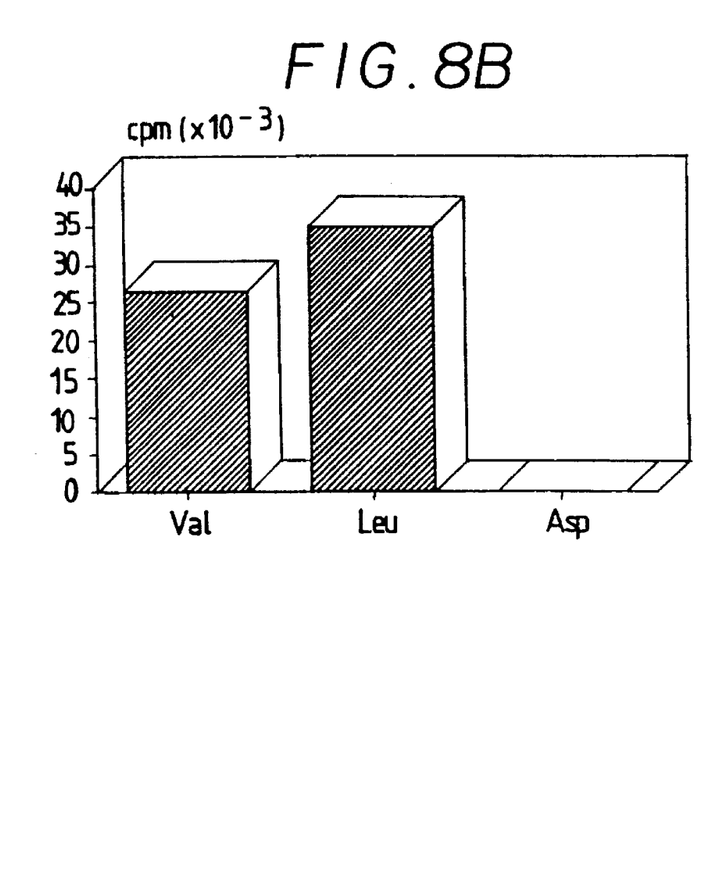

The test is based on the detection for the covalent bond between amino acid and the specific structural domain of the surfactin synthetase. For this purpose, the enzyme was incubated at 37° C. for 30 minutes in the presence of the amino acid marked with the isotope $^{14}$C and the reaction was then interrupted adding TCA at 5%. The proteins precipitated with TCA were then filtered on nitrocellulose filters which, after extensive washing with water to remove the excess amino acid not bound to the enzyme, were counted with a beta counter. The advantage of this test lies in the fact that when the binding reaction of each amino acid in the specificity site of the structural domains of the synthetase is completed, the quantity of radioactivity measured on the filter can be used for a quantitative estimation. For example, the mutant srfAORF2 (4-6) should be able to bind 1 mole of Valine and Leucine per mole of enzyme, whereas no other amino acid should be recognized. The countable quantity of radioactivity on the filter should therefore be comparable when [$^{14}$C] Leucine and [$^{14}$C] Valine are added in the test. Similarly, the preparation of srfAORF1 plus srfAORF2 (4-2-6) should bind with the amino acids Leucine, Valine and Glutamic acid. In addition to this, the quantity of measurable radioactivity when Leucine is added in the test should be 4 times higher than that measurable in the presence of Glutamic Acid and valine. FIG. 8 shows the experimental results obtained.

As can be noted, srfAORF2 (4-6) is no longer capable of binding Aspartic Acid, whereas it maintains its capacity to bind Valine and Leucine in a ratio of about 1:1, showing the complete functionality of the modified enzymatic subunit.

With respect to the preparation containing srfAORF1 and srfAORF2 (4-2-6) the experimental data are perfectly consistent with the fact that srfAORF2 (4-26) has lost its capacity to bind Aspartic Acid and has acquired the capacity to bind a second Leucine. The ratio Leucine:Valine and Leucine:Glutamic Acid is in fact 4:1 and as it is known that two domains binding Leucine are present on srfAORF1, the remaining two must necessarily be present on srfAORF2 (4-2-6).

To complete these data it should be noted that in the enzymatic test used, each time [$^{14}$C] Leucine is added, an equimolar quantity of non-marked Leucine is added. This device is necessary considering the fact that the domains capable of binding Leucine, although to a lesser degree, also recognize Valine. It is therefore necessary to saturate the domains of Leucine with its natural amino acid to avoid over-evaluations in the bond of Valine to the enzyme.

Example 5

In vitro synthesis of surfactin and its analogs.

To demonstrate the functionality of the modified peptide synthetases as described in the preceding examples (mutants SMS349, SMS348 and SMS346) the in vitro synthesis procedure described by Ullrich et al. (1991), Biochemistry, 30: 6503–6508, was followed.

For this purpose the proteinaceous extracts of strains B.subtilis SMS349, B.subtilis SMS348, B.subtilis SMS347, B.subtilis JH642SRF$^+$ (positive control) and B.subtilis SMS352 (negative control) were prepared starting respectively from 4.3, 3.7, 4.1, 4.1 and 3.6 grams of biomass (strain B.subtilis SMS352 is not capable of synthesizing the surfactin synthetase enzyme as it shows a deletion of the promoter responsible for the transcription of the region of DNA coding for the enzyme itself). The cells were resuspended separately in 20 ml of buffer B and lysated as described in example 4.

After centrifugation (30,000 rpm for 20 minutes), streptomycin sulphate (10 mg/ml) was added to the supernatants, containing the soluble proteins, which, after 20 minutes at room temperature, were centrifuged under the same conditions indicated above.

Ammonium sulphate (70% saturation) was added to the supernatants thus obtained and, after allowing the proteins to precipitate at 4° C. for 16 hours, these were collected by centrifugation at 30,000 revs for 30 minutes. The precipitates were collected in buffer B in such volumes as to obtain a final concentration of about 11 mg/ml.

Each proteinaceous extract (100 µl) was added to a solution containing 10 mM ATP, 10 mM $MgCl_2$, 13 mM DTE, 0.1 mM of the following amino acids L-Asp, L-Glu, L-Leu, L-Val and 1 µCi of [$^{14}$C]L-Leu, 80 mM Tris-HCl pH 7.8, 0.8 mM DL-3-hydroxy-tetradecanoyl-CoA, 1.3 mM potassium phosphate and 1 mM EDTA (final volume 0.5 ml).

The DL-3-hydroxy-tetradecanoyl-CoA was synthesized as described by Ullrich et al. (previous reference).

The results shown in table I below clearly indicate that the $^{14}$C-labelled leucine ([$^{14}$C]L-Leu) is incorporated in all cases except for the negative control, in which the surfactin synthetase is not present owing to the deletion of the promotor responsible for the transcription of the operon srfA.

To confirm these data, this experiment was repeated using the proteinaceous extracts of strains SMS352, SMS348 and SMS346 in reaction mixtures to which all four marked amino acids had been added. From table II it is evident that the amino acids L-Leu, L-Val and L-Glu are incorporated in the peptide synthesized by the extracts of SMS348 and SMS346, whereas, as expected, the amino acid L-Asp is not incorporated.

TABLE I

| Strains | incorporated Leucine (cpm) |
| --- | --- |
| SMS352 | 475 cpm |
| JH642 | 643 cpm |
| SMS349 | 571 cpm |
| SMS348 | 2332 cpm |
| SMS346 | 1136 cpm |

TABLE II

| Strains | [$^{14}$C]L-Asp | [$^{14}$C]L-Val | [$^{14}$C]L-Glu | [$^{14}$C]L-Leu |
| --- | --- | --- | --- | --- |
| SMS352 | 0 | 0 | 0 | 0 |
| SMS348 | 0 | 280 cpm | 550 cpm | 2180 cpm |
| SMS346 | 0 | 110 cpm | 250 cpm | 1250 cpm |

We claim:

1. A method for biosynthesizing a novel peptide which comprises:
   (a) constructing a gene encoding a peptide synthetase with an amino acid specificity different than any known peptide synthetase;
   (b) inserting said gene into a vector;
   (c) transforming a microorganism with said vector;
   (d) isolating transformants which express said peptide synthetase; and
   (e) cultivating said transformants to produce said novel peptide.

2. The method of claim 1, wherein in step (a), said gene is obtained by at least one step of:
   deleting one or more activation domain coding regions,
   substituting one or more activation domain coding regions from the same or different peptide synthetase, or
   adding one or more activation domain coding regions from the same or different peptide synthetase.

3. The method of claim 1, wherein said novel peptide has antibiotic, antifungal or immunosuppressive properties.

4. The method of claim 1, wherein said novel peptide comprises the same amino acid residues as surfactin but a different primary sequence.

5. The method of claim 1, wherein said vector is an expression plasmid.

6. The method of claim 1, wherein said vector is an integration plasmid.

7. The method of claim 1, wherein said microorganism is a bacterium, fungus or yeast.

* * * * *